United States Patent [19]
Patterson

[11] Patent Number: 5,906,772
[45] Date of Patent: May 25, 1999

[54] STYRENE-DIVINYL BENZENE COPOLYMER AND STABILIZATION AND ENHANCED DILUTION OF STANDARD TURBIDITY/ NEPHELOMETRY TEST SAMPLES

[76] Inventor: James A. Patterson, 2612 Tanglewood Dr., Sarasota, Fla. 34239

[21] Appl. No.: 09/123,750

[22] Filed: Jul. 27, 1998

[51] Int. Cl.[6] .................................................. G01N 31/00
[52] U.S. Cl. ............................. 252/408.1; 436/8; 436/10; 436/166; 356/243
[58] Field of Search ................................... 436/8, 10, 18, 436/166; 356/243, 356, 339; 252/408.1

[56] References Cited

U.S. PATENT DOCUMENTS

| 4,283,143 | 8/1981 | Patterson | 356/336 |
| 4,291,980 | 9/1981 | Patterson | 356/243 |
| 5,777,011 | 7/1998 | Sadar | 524/253 |

*Primary Examiner*—David A. Redding
*Attorney, Agent, or Firm*—Charles J. Prescott

[57] ABSTRACT

The use of a unique styrene-divinylbenzene copolymer and an improved more highly diluted suspension for preparing standard turbidity test equipment calibration samples of very low turbidity levels for use in the measurement of turbidity in water.

5 Claims, 1 Drawing Sheet

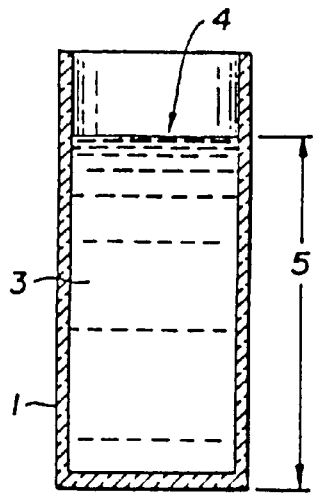
PRIOR ART
Fig.—1.
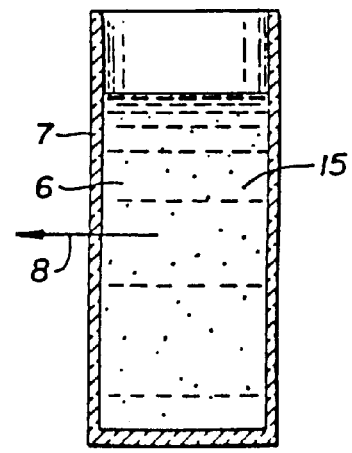
PRIOR ART
Fig.—2.
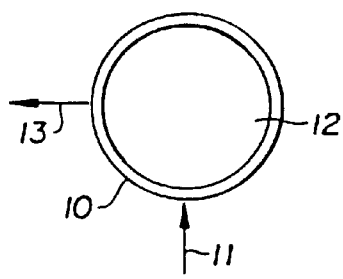
Fig.—3B.
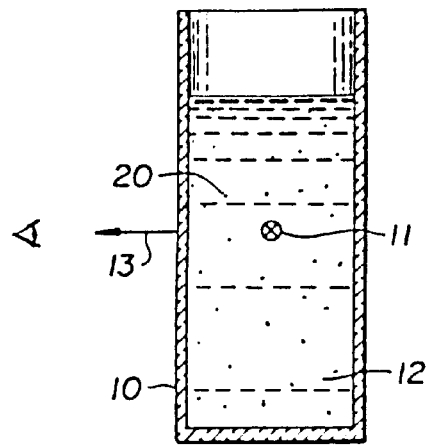
Fig.—3A.

STYRENE-DIVINYL BENZENE COPOLYMER AND STABILIZATION AND ENHANCED DILUTION OF STANDARD TURBIDITY/NEPHELOMETRY TEST SAMPLES

BACKGROUND OF THE INVENTION

1. Scope of Invention

This invention relates generally to the field of turbidity/nephelometry and particularly to an improvement in the stability and accuracy of the test suspension used as test samples to accurately calibrate turbidity/nephelometry measurement equipment.

2. Prior Art

The present invention represents a substantial improvement over my prior teachings as set forth in U.S. Pat. No. 4,291,980. To the extent not reproduced or derived from the '980 patent, that disclosure is incorporated herein by reference.

In testing and treating water for drinking purposes, it is necessary to test the water's Turbidity. Turbidity has a marked effect on the bacteriological quality of water, whether or not disinfection is practiced. This is so because turbidity interferes with the ability to disinfect water.

Turbidity is measured by use of a turbidimeter which includes a light source for illuminating a sample to be tested and one or more photoelectric detectors with a readout to indicate the intensity of light scattered at right angles to the path of the incident light. The greater the scatter, the greater the turbidity. In testing for turbidity, a turbidity reference suspension must be selected which is readily reproducible and which can be used to calibrate the turbidimeter. Until the advent of the '980 patent teaching, no such reference existed.

Prior attempts to measure turbidity were, in retrospect, rather crude. FIG. 1 shows the first accepted means of evaluating turbidity by filling a cylindrical container 1 with water 3 to a height 5. Candle 2 was placed at the bottom of the transparent cylindrical vessel 1. The illumination produced by the candle 2 was viewed downwardly toward the water surface 4. Simply stated, water level 5 was increased until the candle's illumination could no longer be seen at 4. The technique was proposed by Jackson and the height of the water was read in Jackson Turbidity Units (JTU). The result was a crude determination of the turbidity of water for as water became more turbid, the height 5 became smaller for a given sample.

The Jackson method can only be described as primitive at best. The candle would blacken the bottom of the transparent vessel thus interfering with the pure turbidity measurement. Furthermore, sedimentation would precipitate out of solution and would block the candle's illumination, although such sedimentation has nothing to do with turbidity.

The next advance in turbidity measurement involved the use of Formazin suspended in water as the reference. Formazin is the condensation polymer of hydrazine sulfate $(NH_2)_2H_2SO_4$ and hexamethylenetetramine $C_6H_{12}N_4$. Unfortunately, hydrazine compounds are extremely toxic end their use as a preparation of a turbidity standard for water represents certain disposal problems and health problems which should be avoided if possible. A further drawback to the use of Formazin as a standard is that in the 1.0 and 5.0 NTU range, a non-linear dilution of Formazin concentrate is necessary for, in such low concentrations, Formazin decomposes. Formazin is prepared via a standard condensation reaction:

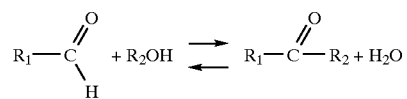

As the Formazin solution becomes more dilute, the reaction is pushed to the left, thus breaking down the compound.

A further drawback experienced through the use of Formazin is that it characteristically has a sedimentary light scatter loss of approximately 10% for four hours. This means that care must be given to thoroughly mix any Formazin suspension prior to sampling. Such a problem can be more readily appreciated by viewing FIG. 2. The turbidity of a Formazin containing standard is done by illuminating transparent cylinder 7 through its base by light source 9. The Formazin 15 suspended in water 6 causes the light to scatter and a light reading is taken at rights angles to the incidence of illumination at 8. The turbidity units are known as Formazin Turbidity Units (FTU). Again, the greater turbidity, the greater the light scatter.

Because of the problems outlined herein, a Formazin standard, although in use for many years, is not at all accurate. The sedimentary light scatter loss is significant and, as was true with regard to the Jackson turbidity test, sediment acts to block the illumination source and results in false readings of the standard. Lastly, Formazin diluted has a life expectancy of approximately one week while in a concentrated form, its life expectancy is approximately 30 days.

It was also found that in order to provide a proper material for use as a standard in turbidity measurements, the particle would have to have an extremely long shelf life and be of a size which would approximate those impurities which normally cause water to be turbid such as spores and bacteriological growth. It was also found necessary to produce a particle which, when suspended in water, would remain suspended for an extremely long period of time so that the turbidity measurement can be taken without sedimentation. All of those necessary characteristics were achieved in producing the specific copolymer of styrene and divinyl benzene of my '980 patent and the present invention. However, the teachings of the '980 patent do not provide for suspension samples at very low levels of turbidity, e.g. below 1.0 NTU and as low as 0.02 NTU.

The production of spherical beads comprised of copolymers styrene and divinylbenzene is well known. For example, see U.S. Pat. Nos. 2,366,007 and 3,463,320. However, until the advent of my '980 patent and as improved upon by the present invention, no material such as a styrenedivinylbenzene copolymer could possibly act as an acceptable standard in turbidity measurement. More specifically, the particle would be spherical in nature and have a diameter approximately in the range of 0.2 microns to 1.0 microns. On a statistical basis, this means that approximately 90% of all beads produced should fall within the range.

There are two basic types of polymerization systems; i.e., suspension and emulsion polymerizations. In suspension polymerization, which is classically an oil in water suspension wherein the oil phase is polymerized by the introduction of free radicals while the oil droplet suspension is maintained, the particles produced tend to have a diameter greater than 1.0 micron. If a classical emulsion polymerization is performed, wherein the polymer is built up from a solubilized phase of monomer, particles much smaller than 0.1 micron are produced. Thus, in order to arrive at an ideal particle size, my former '980 patent developed a unique polymerization process which is a cross between suspension and emulsion polymerization.

The national standard test for turbidity of water is described in ASTM Designation D 1889-94. The currently accepted test equipment for turbidity measurement is the Mixcro 200 BW produced by HF Scientific Corp., a Florida corporation.

Although the turbidity sample standard and method of its preparation disclosed in my '980 patent has also been used recently and has been adopted by the E.P.A as the definitive means for testing the turbidity of water, there remains serious drawbacks to that teaching and the accuracy and reproducibility of test sample suspensions especially below 1.0 NTU. The difficulty with the '980 teaching is with respect to the dilution of the sample to lower NTU units to provide a calibration sample below. The only means for dilution available under the '980 teaching was through the addition of additional Tergitol 4T, a sodium alkyl sulfate anionic pure surface active agent produced by the Union Carbide Company. This addition of 4T prevent the diluted sample from becoming unstable by agglomeration. Although it is accurately claimed in the '980 disclosure that the particles in the test sample remain stable for at least two year, the diluting addition of additional Tergitol 4T may destroy that stability and, more importantly, it becomes virtually impossible to determine the exact gravimetric analysis of the particles because of the presence of the Tergitol 4T which cannot be removed without destroying the sample.

The present invention adds a substantial improvement to the teachings of my previous '980 patent by overcoming these severe limitations of gravimetric analysis inaccuracy through the use of ammonia as a dilutant which is added in sufficient quantity to elevate the pH of the media to an alkaline level of at least about pH 8 or above.

BRIEF SUMMARY OF THE INVENTION

This invention is directed to the use of a unique styrene-divinylbenzene copolymer and an improved more highly diluted suspension for preparing standard turbidity test equipment calibration samples in the measurement of turbidity in water.

It is therefore an object of the present invention to provide a polymeric standard which can be used as a reference suspension for determining much lower levels of turbidity of water without any of the drawbacks in stability or inaccuracy experienced when using the teachings of my previous U.S. Pat. No. 4,291,980.

It is another object of the present invention to prepare a polymeric material which can be used as a standard reference suspension having a shelf life much longer than materials used for the identical purpose in the past and which may be more highly diluted well below that provided by my previous teachings.

It is still another object of the present invention to prepare a polymeric material useful as a standard reference suspension in the measurement of turbidity in water which is non-toxic.

It is yet another object of the present invention to produce a polymeric material useful as a standard reference suspension in measuring the turbidity of water which is stable at extremely low concentrations well below that previously known.

It is still another object of the present invention to produce a polymeric material useful as a substantially more accurately gravimetrically discernible standard reference suspension to measure turbidity in water.

It is still another object of this invention to replace Tergitol T4 as a dilutant after the polymerization reaction with a volatile $NH_3$ as a surface active agent which stabilizes the suspension from agglomeration, provides ammonia gas over the liquid as an anti-biological agent and prevents oxidation of the suspension.

It is still another object of this invention to provide substantially greater accuracy in the gravimetric analysis of the dried residue of particles in testing sample turbidity.

In accordance with these and other objects which will become apparent hereinafter, the instant invention will now be described with reference to the accompanying drawings.

BRIEF DESCRIPTION OF THE DRAWINGS

FIGS. 1 and 2 show prior art tubidimeter.

FIGS. 3A and 3B show turbidimeters according to the '980 teaching and my present invention.

DETAILED DESCRIPTION OF THE INVENTION (The detailed description herebelow has, in part, been reproduced from U.S. Pat. No. 4,291,980 for clarity and convenience).

The use of the present invention as a standard in the measurement of the turbidity of water is shown schematically in FIGS. 3A and 3B. The previously referenced Micro 200 BW turbidimeter. The previously referenced Micro 200 BW turbidimeter has become industry standard test equipment. Turning to FIG. 3A, particles 20 which represent the styrene-divinylbenzene copolymers of the present invention are suspended in extremely pure water 12. Light source 11 which is actually perpendicular to the plane of the drawing strikes substantially transparent cylindrical vessel 10. The suspended copolymers 20 cause particle scatter which is read at right angles to the incident rays shown schematically at 13.

Preparation of Styrene-Divinylbenzene Copolymer Particles

The copolymer particles of the present invention are prepared in a "support phase" which consists of ultrapure water, i.e. water which is at least 10 megohm or better, non-ionic, has no colloidal organic impurities and, finally, has a turbidity of 0.10 NTU or better. If water of such purity is not readily available, a centercut of distilled water can be filtered under a mixed bed deionization column and filtered under high pressure in an MSA packed filter bed. Ideally, a media to monomer ratio should be approximately 10 to 1 by volume but can be as low as 5 to 1.

Monomeric styrene is marked to at extremely high purities (99% pure or better). However, divinylbenzene is traditionally no more than about 52% pure, for pure divinylbenzene tends to be extremely unstable. Some of the impurities found in divinylbenzene are various vinyl-substituted benzenes having the vinyl substitutions in the meta and ortho positions rather than the preferred para position and also products having saturated ethyl groups rather than the unsaturated vinyl groups. Divinylbenzene is also inhibited with approximately 150 ppm of tertiary butyl catachol (TBC). Styrene can also contain some TBC.

As an initial step, both the styrene and divinylbenzene monomers are purified with 6.0N, sodium hydroxide in an extraction process to remove the TBC. The extraction process continues until, on a 10 to 1 monomer to hydroxide basis by volume, there is no color in the hydroxide layer in the separatory funnel.

After the hydroxide extract, the monomer is washed with distilled water three times in the funnel and dried over anhydrous calcium chloride.

Other impurities are removed from the divinylbenzene through the use of silica gel chromatographic purification. More specifically, a one-inch diameter by two-foot stopcock filtered glass column is paced to one-half its height with petroleum ether slurries of chromatographic grade silica gels. After the column is packed, nitrogen is passed therethrough to force out excess petroleum ether. The column is then loaded with the monomer to be purified. Although each monomer can be purified using the silica gel chromatographic purification technique, each monomer should be purified in its own column.

The packed column could handle about ten times its volume of monomers. The flow rate of the monomer through the column should not exceed three-bed (silica gel) volume of monomer per hour. The first bed volume of monomers through the column will contain an excessive amount of petroleum ether and should be set aside for special handling or discarded. The remaining monomers which pass through the column are collected under nitrogen pressure in glass and sealed at approximately –5° C. until used.

The Polymerization Reaction

Surface active agents and surface stabilizing agents are employed in the polymerization process. It is important to select agents which are ionic in nature in order to aid in their removal after the polymerization process is complete. Representative of various surface active agents which are useful in practicing the present invention are purified sodium and potassium alkyl sulfates such as sodium 2-ethylhexyl sulfate and sodium heptadecyl sulfate, the most preferred being Tergitol 4T, a sodium alkyl sulfate anionic pure surface active agent produced by the Union Carbide Company. Proteins can be used as surface stabilizing agents. Examples of acceptable materials are any animal, vegetable or fish proteins which can be solubilized in water, although Knox gelatin powder was found to be perfectly acceptable.

The stabilizing agent is prepared by dissolving, for example, Knox gelatin powder in water to produce a 10% by weight viscous liquid. The liquid is heated to approximately 80° C. and filtered. The filtered protein solution can then be stored until needed.

A free-radical source is needed for the copolymerization reaction. A good free-radical source is benzoyl peroxide. Traditionally, when free-radical polymerization using benzoyl peroxide is carried out, a particle size of approximately 1 micron is achieved. However, it was found that when approximately 0.9% to 20% by weight benzoyl peroxide is used as the free-radical source, the number of free-radical sites for polymerization is increased which results in a decrease in the critical volume of the copolymer.

The polymerization is carried out by starting with a polymer kettle containing distilled water having dissolved therein approximately 1% by weight of the previously prepared surface stabilizing agent and approximately 0.1% by weight of the surface active agent. Nitrogen is used to flush the system for oxygen and acts as a polymerization inhibitor. The mixer is started and the temperature of the solution raised to approximately 85° C. At this point, the monomers are added while rapidly stirring the media.

Characteristically, approximately 500 ml. of the monomer solution is added to a 4.0 liter polymer kettle at a total monomer to media ratio of 1 to 5, that is, a total media volume of 3.0 liters. The monomer mix generally comprises 20% by weight divinylbenzene, 0.9% to 20% by weight benzoyl peroxide, the remainder being styrene. The polymerization is continued under these conditions for approximately thirty minutes during which time microscopic samples of the mix are taken to insure that a proper bead size is being produced. If the mean size distribution of the suspended oil droplets is greater than desired, the size can be reduced by addition of more of the surface active agent. The estimation of size distribution of the oil droplets in suspension must be rapid, since any addition of the surface active agent must remain at least ten minutes in the mixing solution to establish a new equilibrium in the new mean size.

Initially, an oil droplet size of less than 5 microns is tolerable. To achieve a final particle less than $1.0\mu$, surface active agent, preferably Tergitol 4T, is added in an amount of approximately 0.5% by volume media-monomer per micron should the oil droplet be too large. In approximately thirty minutes time, the gel point is reached which causes the solution to increase in viscosity (the gel time being that time in which approximately 30% of the polymerization reaction has been carried out). The temperature is then increased to approximately 95° C. and the mix is refluxed for approximately eight hours at this high temperature with mixing.

After the polymerization is approximately 95–99% complete, the solution is subject to steam distillation which maintains a temperature of approximately 100° C. During the steam distillation process, distilled water is added which results in a removal of any monomer which has not polymerized. The proteins which make up the surface stabilizing agent which remain in solution and on the surface of the polymeric beads are broken down during the steam distillation process into various amino acids. Yield has been increased from about 20% under my '980 patent to in the range of 60 to 80% yield under the present invention.

The solution can then be allowed to cool to approximately 40° C. and is filtered through, for example, a 400 mesh stainless steel screen. The solution can then be passed through a 1 inch by 1 foot mixed bed deionized column at which time the pH of the solution is adjusted to approximately 2.2 through the addition of hydrochloric acid. The low pH further aids in ionization of the amino acids which resulted from a breakdown of the protein. The solution is then passed through a sodium cation column and re-passed through a mixed bed deionized column. In this way, all of the ionic materials such as unreacted stabilizing agents and surface active agents such as Tergitol 4T are collected resulting in a polymeric material which is capable of substantially pure light particle scatter.

The present invention can perform its unique function because the polymeric material is spherical in nature comprising a substantially pure styrene-divinylbenzene copolymer wherein the spherical particle is substantially between 0.2 microns to 1.0 microns in diameter and exhibits substantially pure particle light scatter when suspended in a substantially turbidity-free media having a pH of between 8 and 13 (or more generally having an alkaline pH reading) achieved by the addition of ammonia to the media. The particles of the present invention are also characterized as having a specific gravity substantially between 1.04 and 1.06 which allows for maintenance of a copolymer suspension in pure water.

Polymer Suspension Stability and Dilution

As stated in my previous '980 patent, the polymer particles added to water in suspension at specific concentrations results in stable suspensions in the range of 1.0 to 5.0 NTU and above for at least two years and are used to calibrate turbidimeters as a preliminary necessary step in their use in measuring the turbidity of water.

However, industry demand is for more accurate calibration samples which are well below 1.0 NTU as that is the range of turbidity which is typically encountered in processed drinking water for municipalities. Simply adding pure water to the turbidity suspensions provided by the '980 teachings leads to rapid agglomeration of the particles. Virtually all test samples below 1.0 NTU which were diluted with pure water only showed rapid agglomeration typically in a matter of a few hours. Moreover, the further dilution of the suspension samples further shortened the stability time period before agglomeration occurred.

Under the '980 teaching, the only means for preparing stable sample concentrations substantially below 1.0 NTU includes the addition of Tergitol 4T. The accuracy of each suspension sample must be verified by actual dry measurement of the polymer particles within each particular test sample. This accurate gravimetric analysis is required to be extremely accurate so that sample consistency will be achieved. Where samples have virtually no remaining surface active agent such as Tergitol 4T, the dry weight gravimetric analysis by water evaporation is easily and accurately achievable. However, when additional Tergitol 4T is required to be added to maintain the long-term stability of the test sample in conjunction with water dilution thereof below 1.0 NTU, the removal of the Tergitol 4T during the drying process of the gravimetric analysis is not practical to achieve as the boiling point of the Tergitol 4T is about 400° C., well above the temperature at which the polymer particles themselves will deteriorate. As a result, the dry weight gravimetric analysis of highly diluted stable test samples under the teaching of the '980 application is highly inaccurate because of the remaining presence of the Tergitol 4T in the otherwise dried polymer particles.

The essence of this invention is the utilization of ammonia ($NH_4OH$) an alkalinity of at least pH 8 as a suspension stabilizer for the more highly diluted polymeric sample suspensions below 10 NTU. Test suspension turbidity samples more highly diluted with pure water and raised to an alkaline pH of at least 8 pH through the addition of appropriate amounts of ammonia have been shown to be stable from agglomeration for significant time periods of at least several months. Test samples with as low as 0.02 NTU have been shown to be stable over these lengthy time periods.

In addition to providing suspension stability at much lower turbidity levels, the accuracy in precise gravimetric analysis of the dry weight of the polymer particles within test samples prepared by dilution and pH control by additions of ammonia has been achieved. The ammonia will easily evaporate with the addition of only minimal amounts of heat well below any destructive temperatures of the polymer particles. Because the ammonia is fully evaporated, the gravimetric dry weight analysis of the polymer particles is virtually totally accurate. As a result, the highly repeatable nature of sample preparation at these lower turbidity levels is achieved.

By facilitating extremely accurate gravimetric weight analysis of the polymerization particles which has achieved significantly lower values of NTU, highly accurate calibration curves may also be developed and provided to the user of such samples so that accurate test sample preparation is further achievable. These accurate calibration curves relating the exact weight of polymeric particles to the weight of water as a gravimetric or PPM to water ratio versus true NTU are now provided for the end user.

The free ammonia ($NH_3$) gas in and above the polymer suspension protects it from biological growth which would destroy the particle count from that of the spherical particles. Such biological growth increases the NTU count as the stability test is made. Moreover, the free ammonia gas ($NH_3$) above the polymer suspension is also a gas barrier to the diffusion of oxygen $O_2$ which would react (oxidize) with the polymer resulting in agglomeration of the polymer particles and decrease the NTU measurement.

Suspension Yield

In order to maintain the sample stability of each turbidity sample prepared by the present invention, the dilution level to achieve specific levels of turbidity readings may be easily adjusted by the addition of ammonia ($NH_4OH$) as above described. The amount of additional ammonia is determined by pH measurement, maintaining the pH level on the alkaline side of at least pH 8. Likewise, the dilution may be decreased (or the NTU number increased) by low temperature (70°–90° C.) vaporization of ammonia gas. This is not possible when Tergitol 4T has been added as a stabilizing agent for very low turbidity level samples because Tergitol 4T will not separate or evaporate at such low temperatures. As a result, the yield of useful test sample suspensions under the present invention is substantially increased about 80% versus a 20% yield level when Tergitol 4T is used for stability in more highly diluted, lower turbidity level test samples.

As a secondary benefit of this invention, those skilled in the art can apply the stabilized polymer suspension to accurate aqueous test suspension of unknown NTU and relate those measurements to ppm, ppv, or particle per ml. of aqueous suspensions such as clay suspensions, soil suspensions, latex paints, metal colloids i.e. $AgCL_2$, milk, coffee, soft drinks (coke), alcohol beverages, etc.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:

1. A suspension having an alkaline pH for measuring the turbidity of water comprising:
   a suspension of substantially spherical particles in substantially turbidity-free water;
   said particles comprising substantially pure styrene-divinylbenzene copolymer wherein said spherical particles are substantially between 0.2 $\mu$m to 1.0 $\mu$m in diameter and which exhibit substantially pure particle light scatter when suspended in substantially turbidity-free water;
   a quantity of ammonia sufficient to establish alkalinity of said suspension and to dilute the concentration of said solution.

2. The suspension of claim 1, wherein:
   the concentration of particle is such as to yield a turbidity reading of substantially between 0.02 and 1.0 NTU.

3. The suspension of claim 1, wherein:
   the concentration of particles is such as to yield a turbidity reading of at least about 0.02 NTU.

4. The suspension of claim 1, wherein:

said ammonia is also present as a gas phase with said suspension preventing biological growth and inaccurate or unstable turbidity measurements of said suspension while a quantity thereof is held within a sealed container.

5. The suspension of claim 1, wherein:

said ammonia is also present in a gas phase in said suspension preventing oxidation of said suspension by preventing diffusion of oxygen ($O_2$) into a sealed plastic container holding a quantity of said suspension.

\* \* \* \* \*